United States Patent
Lehmann et al.

(10) Patent No.: US 8,324,913 B2
(45) Date of Patent: Dec. 4, 2012

(54) MOISTURE SENSOR AND METHOD FOR MEASURING MOISTURE OF A GAS-PHASE MEDIUM

(75) Inventors: Mirko Lehmann, Ebnat-Kappel (CH); Heinz-Peter Frerichs, St. Peter (DE); Ingo Freund, Freiburg (DE)

(73) Assignee: Micronas GmbH, Freiburg I. Br. (DE)

( * ) Notice: Subject to any disclaimer, the term of this patent is extended or adjusted under 35 U.S.C. 154(b) by 409 days.

(21) Appl. No.: 12/594,510

(22) PCT Filed: Apr. 2, 2008

(86) PCT No.: PCT/EP2008/002606
§ 371 (c)(1),
(2), (4) Date: Mar. 24, 2010

(87) PCT Pub. No.: WO2008/122390
PCT Pub. Date: Oct. 16, 2008

(65) Prior Publication Data
US 2010/0176826 A1    Jul. 15, 2010

(30) Foreign Application Priority Data
Apr. 5, 2007   (EP) ..................................... 07007171

(51) Int. Cl.
*G01R 27/08*    (2006.01)
*G01N 19/00*    (2006.01)

(52) U.S. Cl. ...................... 324/694; 324/724; 73/335.04
(58) Field of Classification Search .......... 324/691–724; 73/333.04; 257/253
See application file for complete search history.

(56) References Cited

U.S. PATENT DOCUMENTS
4,502,938 A * 3/1985 Covington et al. ........... 204/412
(Continued)

FOREIGN PATENT DOCUMENTS
| DE | 3911812 C2 | 10/1990 |
| EP | 1176418 A2 | 1/2002 |
| EP | 1489408 A1 | 12/2004 |
| WO | 03076921 A2 | 9/2003 |

OTHER PUBLICATIONS

Burgmair et al., "Contribution of the Gate Insulator Surface to Work Function Measurements with a Gas Sensitive FET", Proceedings of IEEE Sensors 2002, IEEE Int. Conf. on Sensors, Jun. 12, 2002, pp. 439-442, vol. 1 of 2. Conf. 1, New York.

(Continued)

*Primary Examiner* — Melissa Koval
*Assistant Examiner* — Farhana Hoque
(74) *Attorney, Agent, or Firm* — Muncy, Geissler, Olds & Lowe, PLLC

(57) ABSTRACT

The invention relates to a moisture sensor which comprises a receiving area on its surface for a moisture film, the layer thickness of which is dependent on the relative humidity in the surrounding of the receiving area. The moisture sensor has a signal source which is connected to at least one control electrode at at least one infeed, the electrode abutting the receiving area, for providing a control voltage to the moisture film. The moisture sensor comprises at least one potential sensor which has at least one sensor area, under the receiving area, which is spaced apart from the at least one infeed. The sensor area is electrically insulated from the receiving area by an insulation layer, located between the sensor area and the receiving area, in such a way that an electrical potential can be capacitively detected by means of the potential sensor, the potential being dependent on the layer thickness of the moisture film and the control voltage.

18 Claims, 3 Drawing Sheets

U.S. PATENT DOCUMENTS

Figure 1:
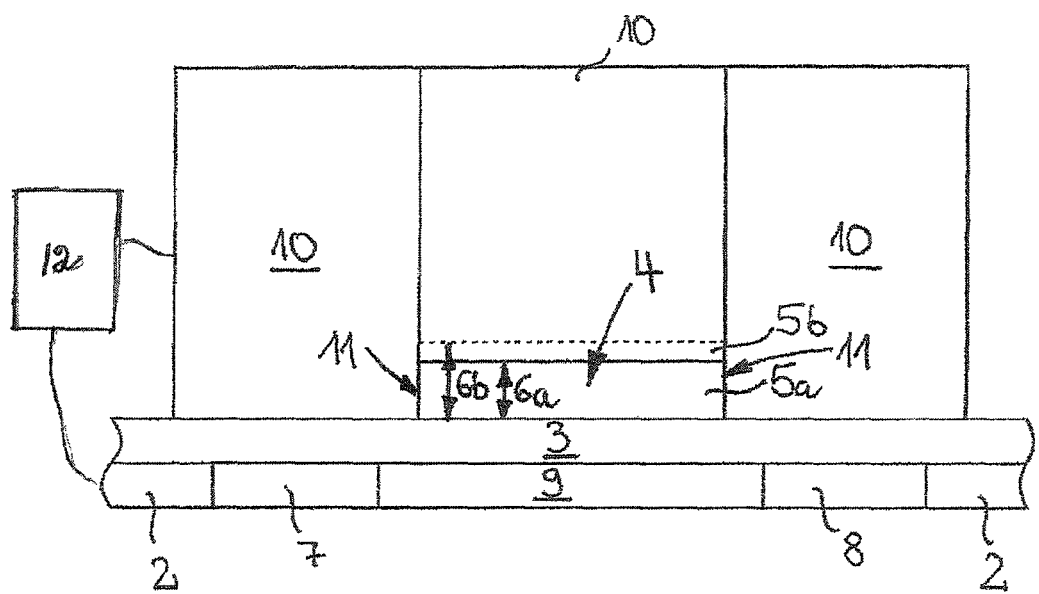

2005/0235735 A1    10/2005    Doll et al.
2006/0096370 A1*    5/2006    Isogai et al. ............... 73/335.04
2006/0249401 A1*    11/2006    Lehmann et al. ............. 205/775

OTHER PUBLICATIONS

Burgmair et al., "Field Effect Transducers for Work Function Gas Measurements: Device Improvements and Comparison of Performance", Sensors and Actuators B, Oct. 15, 2003, pp. 183-188, vol. 95, No. 1-3.

Gee et al., "Hydrophobicity Effects in the Condensation of Water Films on Quartz", Journal of Colloid and Interface Science, Dec. 1990, pp. 450-465, vol. 140, No. 2.

Ruther et al., "Surface Conductivity of CMOS Silicon Nitride Layers", Proceedings of IEEE Sensor 2003, Oct. 22-24, 2003, pp. 920-925.

\* cited by examiner

MOISTURE SENSOR AND METHOD FOR MEASURING MOISTURE OF A GAS-PHASE MEDIUM

The invention relates to a moisture sensor, which has a receiving area on its surface for a moisture film, the layer thickness of which is dependent on the relative humidity in the surrounding of the receiving area, wherein the moisture sensor has a signal source for providing a control voltage to the moisture film which is connected to at least one control electrode at least one infeed, the electrode abutting the receiving area. The invention further relates to a method for measuring moisture of a gas-phase medium, wherein a moisture film, the layer thickness of which is dependent on the relative humidity in the medium, is generated on a solid, and wherein an electric potential is provided to the moisture film at least one infeed. Such a moisture sensor is disclosed in P. Ruther et al.: "Surface Conductivity of CMOS Silicon Nitride Layers," Proceedings of IEEE Sensor 2003, Toronto, Oct. 22-24, 2003, pages 920-925. On the surface of a nitride layer, the moisture sensor has a plurality of ring electrodes concentrically arranged relative to each other, which in each case are spaced apart from each other by gaps. The surface conductivity of the nitride layer, which is dependent on atmospheric moisture, is measured by means of the ring electrodes. To this end, a temporally variable control voltage is provided to the ring electrodes by means of a signal source. On the surface of the nitride layer, the control voltage induces a current flow, which is measured relative to the ambient temperature and the relative humidity and plotted in the form of a grid. The surface conductivity of the nitride layer is determined by means of the current. Furthermore, by means of the grid it is possible to determine the relative humidity from the electric current. However, the moisture sensor has the disadvantage that fouling between the ring electrodes can drastically alter the electrical resistance on the surface of the nitride layer and thus considerably distort the moisture measurement signal.

DE 39 11 812 C2 discloses a moisture sensor which has a moisture-sensitive layer composed of polytetrafluoroethylene, which is located between two electrodes, namely a moisture-permeable cover electrode and a ground electrode. The moisture sensor is used for the capacitive measurement of moisture. This process exploits the effect in which water molecules are adsorbed in microscopic cavities in the amorphous polytetrafluoroethylene and change the capacity between the electrodes relative to the moisture.

DE 39 11 812 C2 further discloses a moisture sensor operating on the resistive measurement principle, wherein the polytetrafluoroethylene layer located between the electrodes is conductive. The electrodes are interdigital comb-shaped electrodes in which the fingers of one electrode are located in the gaps formed between the fingers of the other electrode when the moisture sensor is viewed from above. The electrodes are connected to a voltage source, which induces a current flow in the moisture sensor, wherein the current flows from one of the electrodes via the polytetrafluoroethylene to the other electrode and is measured by means of a sensor.

The same disadvantage of fouling on the electrodes potentially distorting the moisture measurement signal also resides in the moisture sensors disclosed in DE 39 11 812 C2.

The object is therefore to create a moisture sensor and a method of the aforementioned type which make it possible to measure moisture as independently as possible of fouling occurring in the surrounding of the measurement site.

This objective is achieved by a moisture sensor which has a receiving area on its surface for a moisture film, the layer thickness of which is dependent on the relative humidity in the surrounding of the receiving area, wherein the moisture sensor has a signal source with means for generating a control voltage, wherein the signal source for providing the control voltage to the moisture film is connected to at least one control electrode at least one infeed, the electrode abutting the receiving area, wherein the moisture sensor has at least one potential sensor, which has at least one sensor area under the receiving area which is spaced apart from the at least one infeed and which is electrically insulated from the receiving area by an insulation layer located between said sensor area and said receiving area in such a way that an electric potential can be capacitively detected by means of the potential sensor, the potential being dependent on the layer thickness of the moisture film and on the control voltage, wherein an evaluator is connected to the measurement signal output of the potential sensor, wherein the signal source has means for generating a variable control voltage and the evaluator has means for generating a signal that is dependent on the rate at which the potential sensor measurement signal changes in response to the change of the control signal and/or wherein the evaluator has means for generating a signal for a potential shift between the measurement signal of the potential sensor and a reference signal or a reference potential.

The aforementioned object is further achieved by a method for measuring moisture of a gas-phase medium, wherein a moisture film is generated on a solid, the thickness of the film being dependent on the relative humidity in the medium, and wherein an electric potential is provided to the moisture film at least one infeed, wherein at a site spaced apart from the at least one infeed a measurement signal for an electric potential is capacitively measured through an electrical insulation layer, the potential being dependent on the layer thickness of the moisture film and on the control voltage.

In an advantageous manner, an electric potential on the moisture film is measured to determine moisture. The measurement signal is thus largely independent of any fouling that may be present on the control electrode. The thickness of the moisture film is a measurement for the relative humidity in the surrounding, compare Michelle L. Gee et al., "Hydrophobicity Effects in the Condensation of Water Films on Quartz," Journal of Colloid and Interface Science, Vol. 140, No. 2, pages 450-464 (December 1990). The potential on the moisture film can be measured statically and/or dynamically. Due to the charge transfers occurring with dynamic measurement, the measurement signal is dependent on the ohmic resistance of the moisture film and therefore on its thickness in spite of the insulation layer located between the receiving area and the potential sensor. The internal resistance of the signal source is preferably considerably less than the electrical resistance of the fouling on the control electrode that can be expected during the use of the moisture sensor, so that the control voltage provided to the moisture film via the control electrode is minimally affected by the fouling and by an electric current discharged from the fouling.

As moisture decreases, the rate of change of the measurement signal decreases due to the consequently reduced layer thickness and due to the greater electrical resistance of the moisture film when the temporal progression of the control signal remains the same. Analogously, the rate of change increases as moisture increases. The rate of change is therefore a measurement for the relative humidity. The analysis of the rate of change can be carried out using an analog circuit (e.g., a differentiator) and/or with digital signal processing methods. The evaluator used for this purpose can have a microcomputer.

A change in the humidity in the surrounding of the moisture sensor results in a change of the response curve of the ion-sensitive field effect transistor (ISFET), which in turn results in the constant component of the measurement signal increasing in absolute value as relative humidity increases, and decreasing in absolute value as relative humidity decreases. This is brought about by changes in the charge density at the contact surface between the moisture film and the insulation layer. This change in charge density acts as an additional potential on the ISFET channel area or on the input of the measurement amplifier, thus shifting the measurement signal towards potential values greater in absolute value. Therefore, it is also possible to determine the relative humidity statically from the potential shift of the measurement signal. This can be accomplished with, for example, a comparator, an adder, or a subtractor.

It is advantageous if the control electrode has at least two electrode areas connected to each other by at least one strip conductor, and if the receiving area is located between these electrode areas. The measurement signal of the potential sensor is then rendered even more independent of fouling on the control electrode. Not even a short circuit between the electrode areas would cause a change of the measurement signal.

In a preferred embodiment of the invention, the control electrode forms an uninterrupted perimeter around the receiving area and is in particular configured as a ring electrode. Preference is given to the entire inner circumference of the ring electrode being in contact with moisture film in such a way that the latter is charged from all sides with the control voltage.

In an advantageous embodiment of the invention, the potential sensor is a field effect transistor, particularly an ISFET, which has a semiconductor substrate of a first charge carrier type on which are provided a drain and a source of a second charge carrier type, wherein a channel area forming the sensor area is formed between the drain and the source. The field effect transistor then forms an electric capacity with the moisture film across the isolation layer, which capacity is connected in series to the ohmic resistance of the moisture film and to the signal source and on which capacity a voltage drop occurs that changes the conductivity in the channel area of the field effect transistor when the temporally variable control voltage is infed into the control electrode. A high impedance measurement of the potential of the moisture film is possible with the field effect transistor. Preference is given to location of the field effect transistor directly under the moisture film or the receiving area for the moisture film, thus making it possible to obtain a measurement signal that is largely insensitive to electromagnetic interference and a moisture sensor with compact dimensions.

In another embodiment of the invention, preference is given to a laminar measurement electrode for forming the sensor area, the electrode being connected by a strip conductor to the channel area of a field effect transistor and/or to an input of a high-impedance measurement amplifier. In this manner the channel area or the measurement amplifier can also be laterally spaced apart from the sensor area.

It is advantageous if the clear space between two electrode areas located on both sides of the receiving area or the clear width of the ring electrode is smaller than 100 μm, particularly smaller than 10 μm, and preferably smaller than 1 μm. For most applications, this dimensioning enables the measurement signal to react to a change in moisture with sufficient speed. With a ring electrode clear width of ca. 1 μm, the time required for the sensor to detect a stepwise change in relative humidity from 5% to 95% is between ca. 0.1 and 2 seconds.

In an advantageous embodiment of the invention, the signal source is configured in such a way that it can generate a control voltage with at least one jump discontinuity, particularly a rectangular signal. The high rate of change of the signal at the jump discontinuity results in a rapid change of the measurement signal in response to the jump discontinuity. Furthermore, the rate of change and the potential shift of the measurement signal in response to a change in humidity can be easily determined by means of the jump discontinuity of the measurement signal.

Preference is given to the insulation layer consisting of a silicone dioxide layer and/or a silicone nitride layer. These layers enable a high specific electrical resistance and are easily manufactured with standard semiconductor production processes.

It is advantageous if the signal source, the control electrode, the potential sensor, the insulation layer, and the evaluator are integrated in a semiconductor chip. The moisture sensor can then be economically mass produced using semiconductor manufacturing techniques, and furthermore it can be manufactured with compact dimensions. The semiconductor chip can be coated with an electrically insulating sealing compound, which has an opening that forms an access to the receiving area.

Other advantageous embodiments of the invention are described in the dependent claims.

Figure 2:
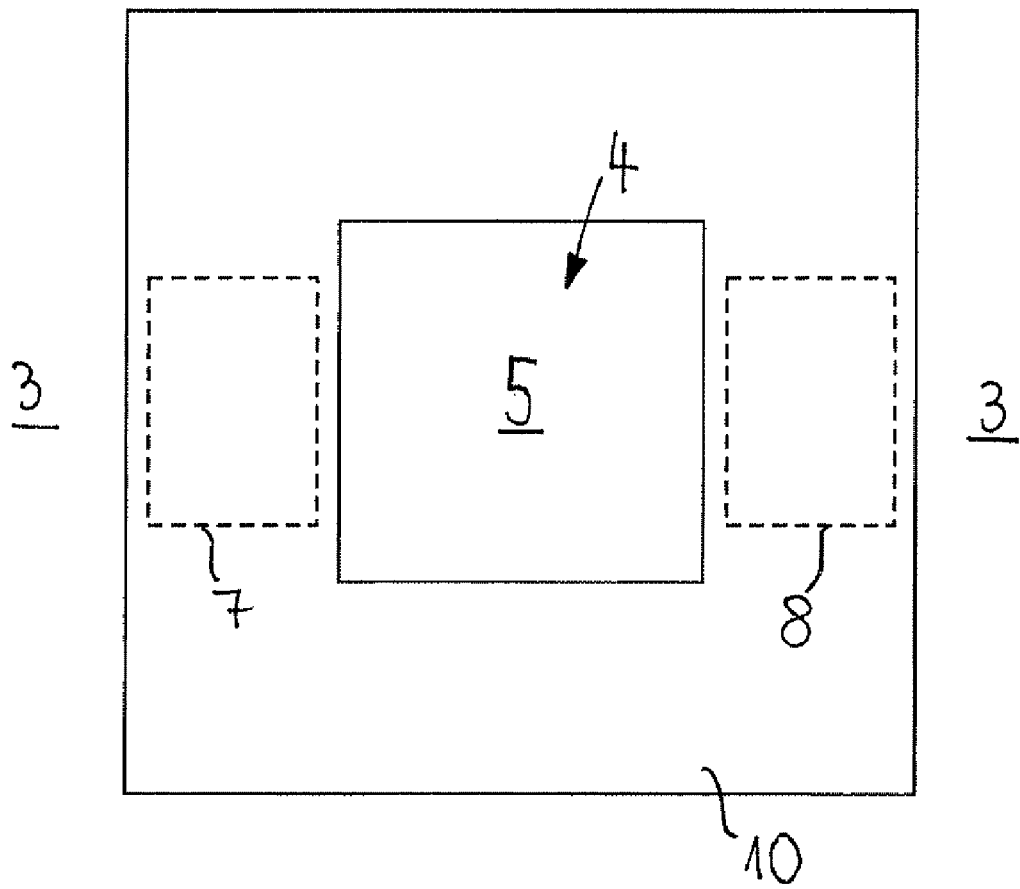
Figure 3:
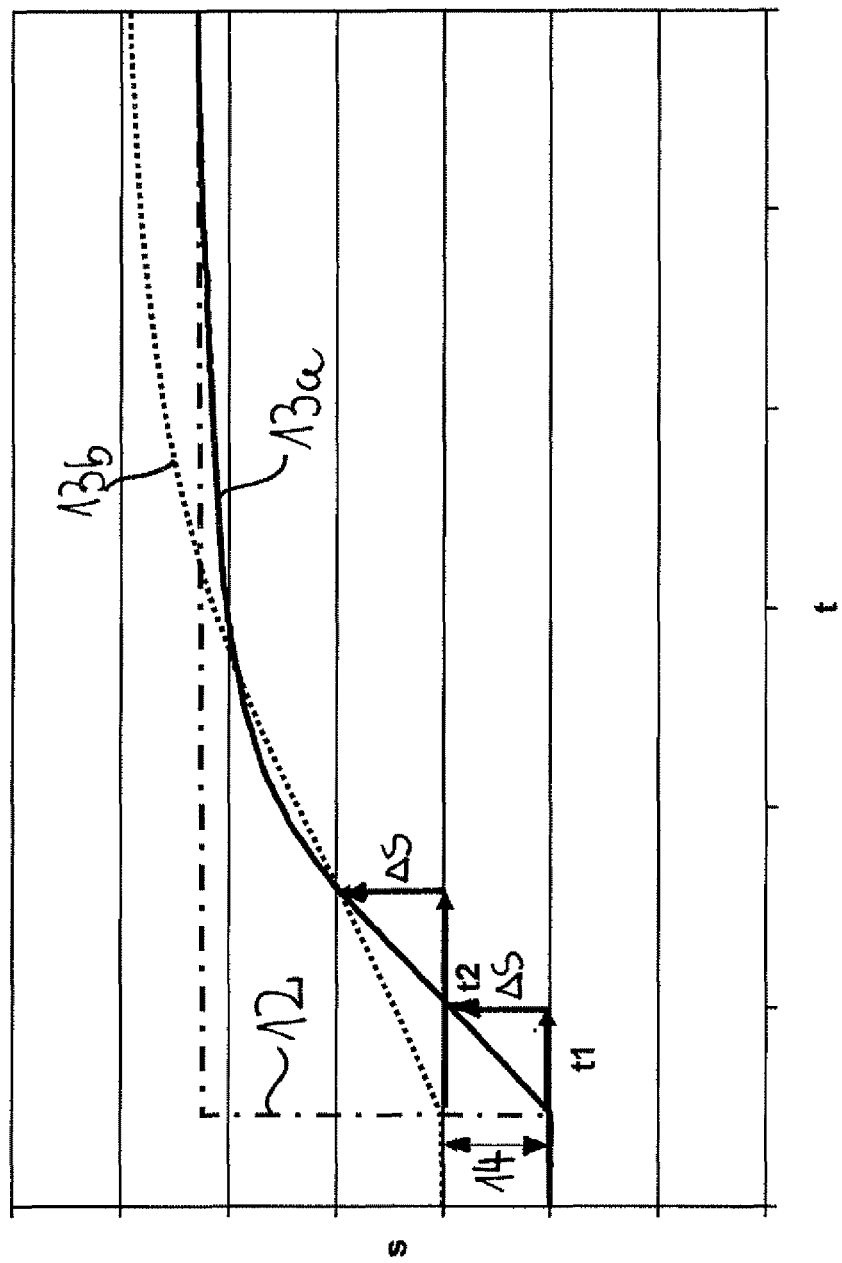

An illustrative embodiment of the invention is explained in detail in the following, with reference to the drawing. Shown are:

FIG. 1 a partial cross-section of a moisture sensor comprising a control electrode for providing a control voltage to a moisture film, FIG. 2 a view from above of a section of a semiconductor chip of the moisture sensor, in which the control electrode and an ISFET located under the electrode can be discerned, and FIG. 3 a graphic illustration of two measurement signals of a potential sensor of the moisture sensor plotted at different relative humidities and of a control voltage provided to the moisture film, wherein the time t is plotted on the x-axis and the measurement signal amplitude s is plotted on the y-axis.

A moisture sensor designated in its entirety by 1 in FIG. 1 has a semiconductor substrate 2, on the surface of which is located an electrical insulation layer 3, preferably a silicone dioxide layer or a silicone nitride layer. A doping of a first charge carrier type is inserted in the semiconductor substrate 2.

A receiving area 4 for a moisture film 5*a*, 5*b* is provided on the insulation layer 3. The moisture sensor 1 is extrusion-coated with an electrically insulating sealing compound, which is not shown in any greater detail in the drawing and which has an opening forming an access to the receiving area. The layer thickness 6*a*, 6*b* of the moisture film 5*a*, 5*b* and thus the ohmic resistance of the moisture film 5*a*, 5*b* are dependent on the relative humidity of the atmosphere in contact with the receiving area 4. This is indicated by a dashed line in FIG. 1.

In the semiconductor substrate 2 is integrated a potential sensor, which has a sensor area 9 under the receiving area for detecting electric charges in the vicinity of the receiving area. The potential sensor is configured as an ISFET and comprises a drain 7 and a source 8 of a second charge carrier type. Between the drain 7 and the source 8 is located a channel area, which forms the sensor area 9. The channel area is spaced apart from the receiving area 4 or the moisture film 5*a*, 5*b* located therein by the insulation layer 3.

On its surface facing away from the channel area, the moisture sensor 1 has a control electrode 10, which is in contact with the outer edge of the moisture film serving as an infeed 11 for a control voltage. The infeed 11 is located on top of the rim of the channel area or laterally spaced apart from it. In FIG. 2 it can be discerned that the control electrode 10 is configured as a ring electrode and defines the receiving area 4 for the moisture film 5a, 5b. Sections of the control electrode 10 are located on top of the source 8 and the drain 7. The control electrode 10 is electrically insulated from the source 8 and the drain 7 by the insulation layer 3.

The control electrode 10 is electrically connected by a strip conductor to a first output terminal of a signal source 12. A second output terminal of the signal source 12 is joined to the semiconductor substrate 2. Preference is given to integration of the signal source in the semiconductor substrate.

By means of the signal source, a temporally variable control voltage, namely a rectangular signal having a predetermined frequency and a predetermined amplitude, is generated and provided via the control electrode 10 to the moisture film 5a, 5b. The temporal progression 12 of the control voltage is graphically illustrated in FIG. 3. With the ISFET, the moisture film 5a, 5b forms an electric capacity, which is connected in series to the ohmic resistance and the control electrode.

While the control voltage is residing on the moisture film 3, the electric potential in the receiving area 4 is capacitively detected by means of the ISFET. The measurement signal 13a, 13b of the ISFET is dependent on the temporal progression 12 of the control voltage and on the layer thickness 6a, 6b of the moisture film 5a, 5b. The layer thickness 6a, 6b can be smaller than 500 nm and is preferably smaller than 100 nm.

In FIG. 3 it can be discerned that with an unchanging progression 12 of the control voltage, the rate at which the measurement signal 13a, 13b changes in response to a change in the control voltage decreases as the thickness of the moisture film decreases. The value of this rate of change can be determined, for example, by measuring the time $t_1$ or $t_2$ that the measurement signal 13a, 13b needs to change its value by a predefined magnitude $\Delta s$ when a jump discontinuity occurs in the control voltage and by calculating the rate of change from the quotients $\Delta s/t_1$ or $\Delta s/t_2$.

In FIG. 3 it can be further discerned that with an unchanging progression 12 of the control voltage, the measurement signal 13a, 13b shifts by an offset 14 if the layer thickness 6a, 6b of the moisture film 5a, 5b, and thus the relative humidity, changes. As the layer thickness 6a, 6b increases the magnitude of the measurement signal 13a, 13b increases, and as the layer thickness decreases the magnitude of the measurement signal 13a, 13b decreases.

Reference values relative to the relative humidity are provided for the rate of change and the offset 14; these values can be in the form of response curves or in the form of a grid for which reference points are stored. Preference is given to determination of the reference values by measurement; however, they can also be calculated, compare Michelle L. Gee et al., "Hydrophobicity Effects in the Condensation of Water Films on Quartz," Journal of Colloid and Interface Science, Vol. 140, No. 2, pages 450-464 (December 1990), incorporated herein by reference.

By means of the potential sensor measurement signal 13a, 13b and the reference values, it is then possible to determine the relative humidity in order to generate, for example, an analog signal and/or a corresponding digital signal proportional to the relative humidity. To this end, a measurement signal output of the potential sensor is connected to a suitable evaluator. This evaluator has an electric circuit for generating a signal for the rate of change and a signal for the offset 14 of the measurement signal 13a, 13b.

The invention claimed is:

1. A moisture sensor comprising:
    a receiving area retaining a moisture film, wherein a thickness of said moisture film is a function of relative humidity surrounding the receiving area;
    a signal source configured to generate a control voltage, wherein the signal source provides a control voltage to the moisture film and is connected to at least one control electrode having at least one infeed connected to the moisture film, the control electrode abutting the receiving area;
    at least one potential sensor, having at least one sensor area positioned under the receiving area, said potential sensor being spaced apart from the at least one infeed and being electrically insulated by an insulation layer located between said sensor area and said receiving area, whereby said potential sensor capacitively detects an electric potential which is a function of the layer thickness of the moisture film and the control voltage;
    an evaluator connected to the measurement signal output of the potential sensor, wherein (a) the signal source is configured to generate a variable control voltage and the evaluator is configured to generate a signal dependent on the rate at which the potential sensor measurement signal changes in response to the change of the control signal and/or (b) the evaluator is configured to generate a signal for a potential shift between the measurement signal of the potential sensor and a reference signal or a reference potential.

2. The moisture sensor according to claim 1, wherein the control electrode has at least two electrode areas connected to each other by at least one strip conductor, and wherein the receiving area is located between these electrode areas.

3. The moisture sensor according to claim 1, wherein the control electrode forms an uninterrupted perimeter around the receiving area.

4. The moisture sensor according to claim 3, wherein the control electrode is a ring electrode.

5. The moisture sensor according to claim 1, wherein the potential sensor is a field effect transistor, which has a semiconductor substrate of a first charge carrier type on which a drain and a source of a second charge carrier type is arranged, and wherein a channel area forming the at least one sensor area is formed between the drain and the source.

6. The moisture sensor according to claim 5, wherein the field effect transistor is an ion sensitive field effect transistor.

7. The moisture sensor according to claim 1, wherein the at least one sensor area is a laminar measurement electrode connected by a strip conductor to the channel area of a field effect transistor and/or to an input of a high-impedance measurement amplifier.

8. The moisture sensor according to claim 1, wherein a space between two electrode areas located on both sides of the receiving area or the clear width of the ring electrode is smaller than 100μm.

9. The moisture sensor according to claim 8, wherein the space is smaller than 10μm.

10. The moisture sensor according to claim 9, wherein the space is smaller than 1μm.

11. The moisture sensor according to claim 1, wherein the signal source is configured to generate a control voltage with at least one jump discontinuity.

12. The moisture sensor according to claim 11, wherein the control voltage is a rectangular signal.

13. The moisture sensor according to claim 1, wherein the insulation layer includes a silicone dioxide layer and/or a silicone nitride layer.

14. The moisture sensor according to claim 1, wherein the signal source, the control electrode, the potential sensor, the insulation layer, and the evaluator are integrated in a semiconductor chip.

15. A method for measuring moisture of a gas-phase medium, the method comprising:
providing a moisture film having a thickness which is a function of relative humidity in the medium is on a solid;
providing an electric potential to the moisture film by at least one infeed; and
capacitively measuring, at a site spaced apart from the at least one infeed, a measurement signal for an electric potential through an electrical insulation layer, the potential being dependent on the layer thickness of the moisture film and on the control voltage.

16. The method as in claim 15, wherein a temporally variable electric potential is provided to the moisture film.

17. The method as in claim 15, wherein a rate at which the electric potential changes in response to a change of the control signal is determined.

18. The method as in claim 15, wherein a potential shift between the measured electric potential and a reference potential is determined.

* * * * *